United States Patent [19]

Park et al.

[11] Patent Number: 4,973,329
[45] Date of Patent: Nov. 27, 1990

[54] ASSEMBLY OF WIRE INSERTER AND LOCK FOR A MEDICAL WIRE

[75] Inventors: Harry Park; Udi Fishman, both of Santa Clara, Calif.

[73] Assignee: Medical Innovations Corporation, Milpitas, Calif.

[21] Appl. No.: 399,578

[22] Filed: Aug. 26, 1989

Related U.S. Application Data

[63] Continuation of Ser. No. 193,945, May 16, 1988, Pat. No. 4,860,942.

[51] Int. Cl.$^5$ .............................................. A61M 17/00
[52] U.S. Cl. ........................................ 606/1; 128/657; 604/159
[58] Field of Search ................ 128/657, 778; 604/164, 604/159; 226/127, 130; 606/1

[56] References Cited

U.S. PATENT DOCUMENTS

| | | | |
|---|---|---|---|
| 3,682,173 | 8/1972 | Center | 604/159 |
| 4,253,462 | 3/1981 | Ducher et al. | 128/303 R |
| 4,326,520 | 4/1982 | Alley | 604/159 |
| 4,349,023 | 9/1982 | Gross | 604/164 |
| 4,598,708 | 7/1986 | Beranek | 128/303 R |
| 4,726,369 | 2/1988 | Mar | 128/303 R |

*Primary Examiner*—Stephen C. Pellegrino
*Attorney, Agent, or Firm*—Willie Krawitz

[57] ABSTRACT

An assembly of a wire inserter and lock is provided. The assembly includes a body portion with a bore inlet and outlet aligned with a locking area and an elongate outlet to align the wire as it passes therethrough.

A spring loaded locking button is mounted within the body and defines two tear-shaped bores through which the wire passes. In the locked position, the wire is wedged into the narrow ends of the tear-shaped bores, and this provides sufficient force to lock the wire without damage.

The body portion may include notched areas around which the wire can be wound, and a hole for capturing the end of the wire to facilitate storage of the wire.

20 Claims, 2 Drawing Sheets

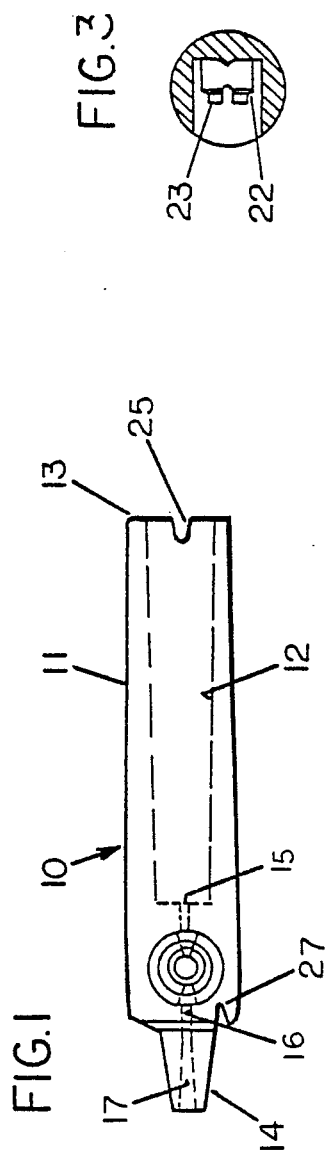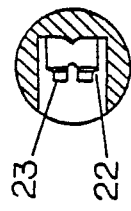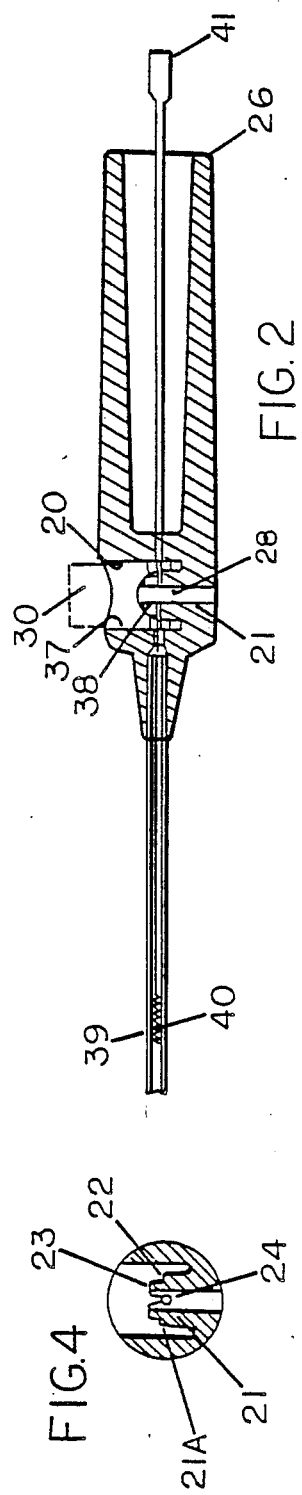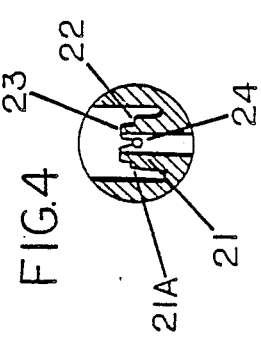

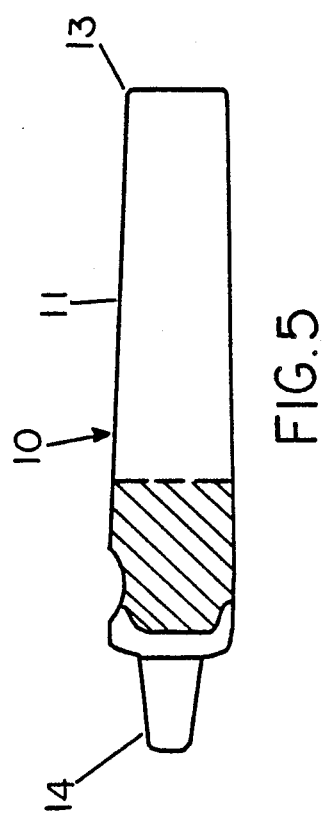
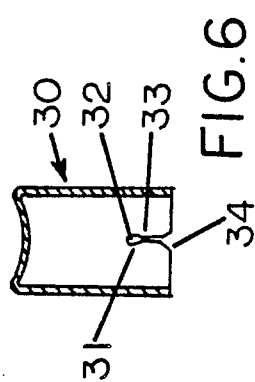

4,973,329

ASSEMBLY OF WIRE INSERTER AND LOCK FOR A MEDICAL WIRE

This is a continuation of copending application(s) Ser. No. 7/193,945 filed on May 16, 1988 now U.S. Pat. No. 4,860,942.

BACKGROUND OF THE INVENTION

This invention relates to an assembly of a length adjustable wire inserter, including a wire, and a lock therefor.

In many medical applications, a wire is employed for insertion into a catheter for stiffening and guiding purposes, for inserting medical devices, probes, detectors, etc., through a catheter into a patient, or for direct insertion into a patient. It is important for the physician to operate these devices with one hand, even when wearing surgical gloves, and to advance the wire inserter in a reasonably aligned manner with the direction of the device.

Also, it is important that following advancement of the wire, it can then be locked in place with a minimum effort, and without requiring use of a locking screw, or similar non-sanitary device.

In addition, when the wire is locked, the locking force should not deform or damage the wire, and when in use, the wire will not escape from its housing.

THE INVENTION

According to the invention, an assembly of a wire inserter and lock for medical wire is provided, comprising a housing for the wire, and a spring loaded, push button lock for the wire. The push button includes opposed, wedge-shaped locking holes through which the wire passes. In the locked position, the wedge portions of the locking holes are biased against the wire and lock the wire in place. When the push button is depressed, the wire moves out of contact with the wedge portions of the holes and can move freely backwards or forwards, to allow adjustability for length.

Preferably, the housing for the wire provides entry and exit bores for the wire which are aligned with the locking holes of the push button, and are also aligned with a protective outlet bore nozzle of the housing. This alignment feature facilitates alignment of the wire when it is advanced or retracted.

BREIF DESCRIPTION OF THE DRAWINGS

FIG. 1 is a top plan view of the device in axial section;

FIG. 2 is a side elevation view in axial section of the device taken along lines B—B of FIG. 1;

FIG. 3 is a cross section view taken along lines A—A of FIG. 1;

FIG. 4 is a cross sectional view taken along lines C—C of FIG. 1;

FIG. 5 is a cross sectional view taken along lines D—D of FIG. 1; and,

FIG. 6 is an external view in side elevation of the push button;

DESCRIPTION OF THE PREFERRED EMBODIMENTS

The assembly 10 of a wire inserter and lock for a medical wire of this invention is shown in FIG. 1, and comprises a housing member 11, preferably of injection molded plastic defining a cavity portion 12, distal end 13, and a proximal nozzle 14. Aligned entry and exit bores 15, 16 are defined in the interior of the housing, and are aligned with an outlet bore 17 in the nozzle. The nozzle taper enables engagment with the entry bore of a catheter. If desired, the housing may be constructed of metal.

A push button cavity 20 is defined within the housing, and a spring support and wire alignment riser 21 is integrally formed within the cavity and spaced 21a from the wall of the housing cavity. The riser 21 includes a washer and spring support 22 and a central, circular washer and spring locater 23. A central slot 24 is defined on the washer support 22 along which the wire can move. The slot 24 is axially aligned with the entry and exit bores 15, 16 and outlet bore 17 of the nozzle 17, and this arrangement permits a reasonably linear and alignment movement of the wire through the assembly 10.

The housing member 11 defines notches 25, 26 and 27 around which the wire is wound, when not in use. A bore 28 is defined on the housing for insertion of a tail end element (infra) of the wire to secure the wire around the notches. This facilitates packaging, shipping and handling the device prior to use.

The hollow push button 30 is shown in FIG. 6, and is manufactured of a typical stainless steel, such as 304, and defines radially, opposed locking holes, one hole 31 being shown. The locking holes are tear-shaped and define upper, rounded portions 32 and lower, wedge-shaped portions 33. The specific configurations of the wedge portions 33 can be predetermined depending on the amount of pressure to be applied to the wire. Radially opposed notches, one notch 34 being shown, are defined on the push button. When the push button is positioned within the push button cavity 20, the notches 34 are aligned along the slot 24 of the riser 21.

During assembly of the device, a biasing spring 37, washer 38 and the push button 30 are loaded onto the riser 21. A guide wire 39 is then threaded through the outlet bore 17, exit bore 16, locking holes 31 of the push button, and then passed along the central slot 24, and out the inlet bore 15. The wire 39 may be constructed of plastic or of a braided, medical grade stainless steel material, etc. A spring tip 40 is attached to the end of the wire and functions to avoid puncturing a vein, organ, etc., of the patient, although in some cases, a spring tip is not necessary. The spring tip is preferably sized slightly larger than the exit bore 16, so it will not slip out of the housing. When not in use, the tip of the wire is positioned within the outlet bore of the nozzle for purposes of protection. A tail end plug 41 is provided for insertion into the bore 28 to secure the wire for storage purposes following winding around the notches 25, 26 and 27.

In the locked position, the spring loaded push button 30 is biased upwardly, but secured in place by the guide wire 39 which is compressed into the wedge-shaped portions 33 of the locking holes 31, and also along the entry and exit bores 15 and 16. Thus, four support points are provided along the guide wire, and this produces a more secure locking action.

When the push button 30 is depressed into the space 21a between the riser 21 and the housing, the locking holes will move downwardly, and the compression contact on the guide wire 39 will be removed. The guide wire will then pass freely along the rounded portions 32 of the holes 31, and the wire can then be advanced or retracted freely.

It will be appreciated that the device can be manipulated using only one hand, even when wearing a surgical glove, and this enables a surgeon to manipulate the wire with one hand, and control the locking function using only the other hand.

Finally, the device of this invention can be easily manufactured and assembled, and it can be easily stored, packaged, and shipped.

We claim:

1. An assembly of a wire inserter, and a lock for a medical wire, comprising:
   a. a housing;
   b. a push button cavity defined by the housing;
   c. wire alignment means defined within the cavity;
   d. a biased push button mounted within the cavity, and defining at least one alignment bore aligned with the wire alignment means and shaped to lock with the medical wire; and,
   e. a medical wire mounted for movement along the alignment means, and through the alignment bore; whereby:
      i. when the push button is biased in one direction, it will compress the medical wire into the alignment bore, and thereby lock the wire into the alignment bore, and thereby lock the wire against movement therethrough; and,
      ii. when the push button is releasably biased in another direction, the medical wire will be unlocked from the alignment bore, thereby enabling the medical wire to be adjustable released therefrom for free, linear movement through the housing, without damage to the wire.

2. The assembly of claim 1, in which the push button is adapted to be manipulated with one hand, and the wire is adapted to be manipulated with the other hand.

3. The assembly of claim 2, in which the wire alignment means includes an alignment slot along which the medical wire is adapted for movement.

4. The assembly of claim 3, in which two alignment bores are provided by the push button, for engagement with the medical wire.

5. The assembly of claim 4, in which outward biasing of the push button will compress and lock the medical wire into the wedge-shaped alignment bores, and inward pressure applied to the push button will unlock the medical wire from the alignment bores.

6. The assembly of claim 5, in which the push button is mounted on a riser element, and defines radially opposed bores, including the wedge-shaped portions aligned with the alignment slot.

7. The assembly of claim 6, in which an exit bore is defined by the housing at one end of the alignment slit, and an entry bore is defined at an opposed end from the exit bore, the exit and entry bores, and alignment slot being aligned.

8. The assembly of claim 7, in which the housing defines a proximal nozzle portion having an outlet bore for the wire aligned with the exit and entry bores, the proximal nozzle being sized and shaped for engagement with an entry bore of a catheter.

9. An assembly of a wire inserter, and a lock for a wire, comprising:
   a. a housing;
   b. a button cavity defined by the housing;
   c. a biased button mounted within the cavity and defining at least one alignment edge lock and shaped to align with the said wire; and,
   d. a wire mounted for movement along the alignment edge lock; whereby:
      i. when the button is biased in one direction, it will compress the wire along the alignment edge lock; and,
      ii. when the button is releasably biased in an opposite direction, the wire will be unlocked from the alignment edge lock, thereby enabling the wire to be adjustably released therefrom for free, linear movement through the housing, without damage to the wire.

10. The assembly of claim 9, including a push button adapted to be manipulated with one hand, and a medical wire adapted to be manipulated with the other hand.

11. The assembly of claim 9, in which the alignment edge lock includes an alignment slot along which the medical wire is adapted for movement.

12. The assembly of claim 10, in which two wedge-shaped alignment bores are provided by the push button for engagement with the medical wire.

13. The assembly of claim 12, in which outward biasing of the push button will compress and lock the medical wire into the wedge-shaped alignment bores, and inward pressure applied to the push button will unlock the medical wire from the alignment bores.

14. The assembly of claim 12, in which the push button is mounted on a riser element, and defines radially opposed bores, including the wedge-shaped bores aligned with the alignment slot.

15. The assembly of claim 14, in which an exit bore is defined by the housing at one end of the alignment slot, and an entry bore is defined at an opposed end from the exit bore, the exit and entry bores, and alignment slot being aligned.

16. The assembly of claim 15, in which the housing defines a proximal nozzle portion having an outlet bore for the wire aligned with the exit and entry bores, the proximal nozzle being sized and shaped for engagement with an entry bore of a catheter.

17. An assembly of a wire inserter, and a lock for a wire, comprising:
   a. a housing;
   b. a button cavity defined by the housing;
   c. a button mounted within the cavity and defining at least one alignment lock means shaped to align with the said wire; and,
   d. a wire mounted for movement along the alignment lock means; whereby:
      i. when the button is moved in one direction, it will compress the wire with the alignment lock means; and,
      ii. when the button is moved in an opposite direction, the wire will be unlocked from the alignment lock means, thereby enabling the wire to be adjustably released therefrom for free, linear movement through the housing, without damage to the wire.

18. The assembly of claim 17, is which the wire is a medical wire.

19. The assembly of claim 18, in which the button is a biased push button.

20. The assembly of claim 17, in which the button is adapted to be manipulated with one hand, and the wire is adapted to be manipulated with the other hand.

* * * * *